US00PP11173P

United States Patent [19]

Vega

[11] Patent Number: Plant 11,173

[45] Date of Patent: Jan. 4, 2000

[54] AVOCADO TREE NAMED 'MENDEZ NO. 1'

[76] Inventor: Carlos Mendez Vega, 2 Privada de Bruselas, #60 Col la Joyita, Uruapan, Michoacan, Mexico, CP60170

[21] Appl. No.: 08/959,629

[22] Filed: Oct. 22, 1997

[51] Int. Cl.[7] ..... A01H 5/00

[52] U.S. Cl. ..... Plt./200

[58] Field of Search ..... Plt./44, 200

*Primary Examiner*—Howard J. Locker
*Assistant Examiner*—Melissa L. Kimball
*Attorney, Agent, or Firm*—Kelly Bauersfeld Lowry & Kelley, LLP

[57] ABSTRACT

A new and distinct variety of an avocado tree having many characteristics similar to those of 'Hass' that is characterized by profuse blooming six to seven months earlier than the 'Hass' avocado tree and bearing fruit that is mature earlier during the season than 'Hass' fruit.

6 Drawing Sheets

BACKGROUND OF THE INVENTION

This invention relates to a new and distinct variety of an avocado tree having many characteristics similar to that of 'Hass'. The invention is characterized by profuse blossoming six to seven months earlier than the 'Hass' avocado tree and bearing fruit that is mature earlier during the season than 'Hass' fruit.

SUMMARY OF THE INVENTION

The tree is the result of an unpatented sport discovered by the observation of its early flowering in relation to the 'Hass' avocado, by Carlos Mendez Vega in the orchard named "Cherangueran" in the Municipality of Uruapan, Michoacan, Mexico. An asexual reproduction of the tree was made by removing a bud bearing stick from the sport and grafting it onto an existing two year old Mexican Criollo avocado tree. The resulting grafting tree, after the scion had grown out, bore fruit of the same variety as the sport and with the same schedule of maturity.

In California, 'Mendez No. 1' avocado trees have been planted and grown on Cheravo Ranch, 3430 Ojai Road, Santa Paula, Calif.

BRIEF DESCRIPTION OF THE DRAWINGS

The accompanying photographs show the tree and fruit of the present invention. In such photographs.

BOTANICAL DESCRIPTION OF THE PLANT

Figure 1:
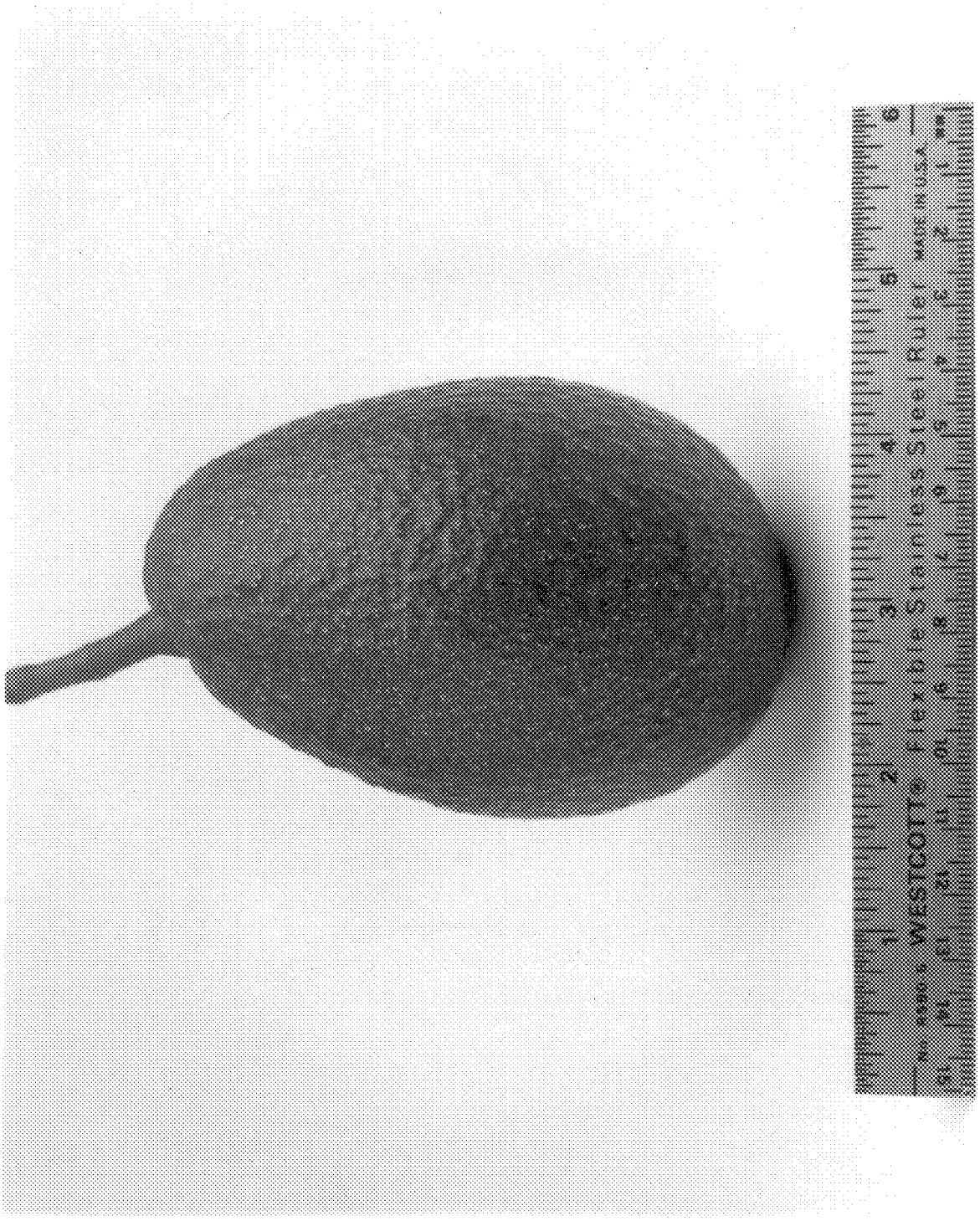
FIG. 1 shows an exterior view of the mature fruit of 'Mendez No. 1'.
Figure 2:
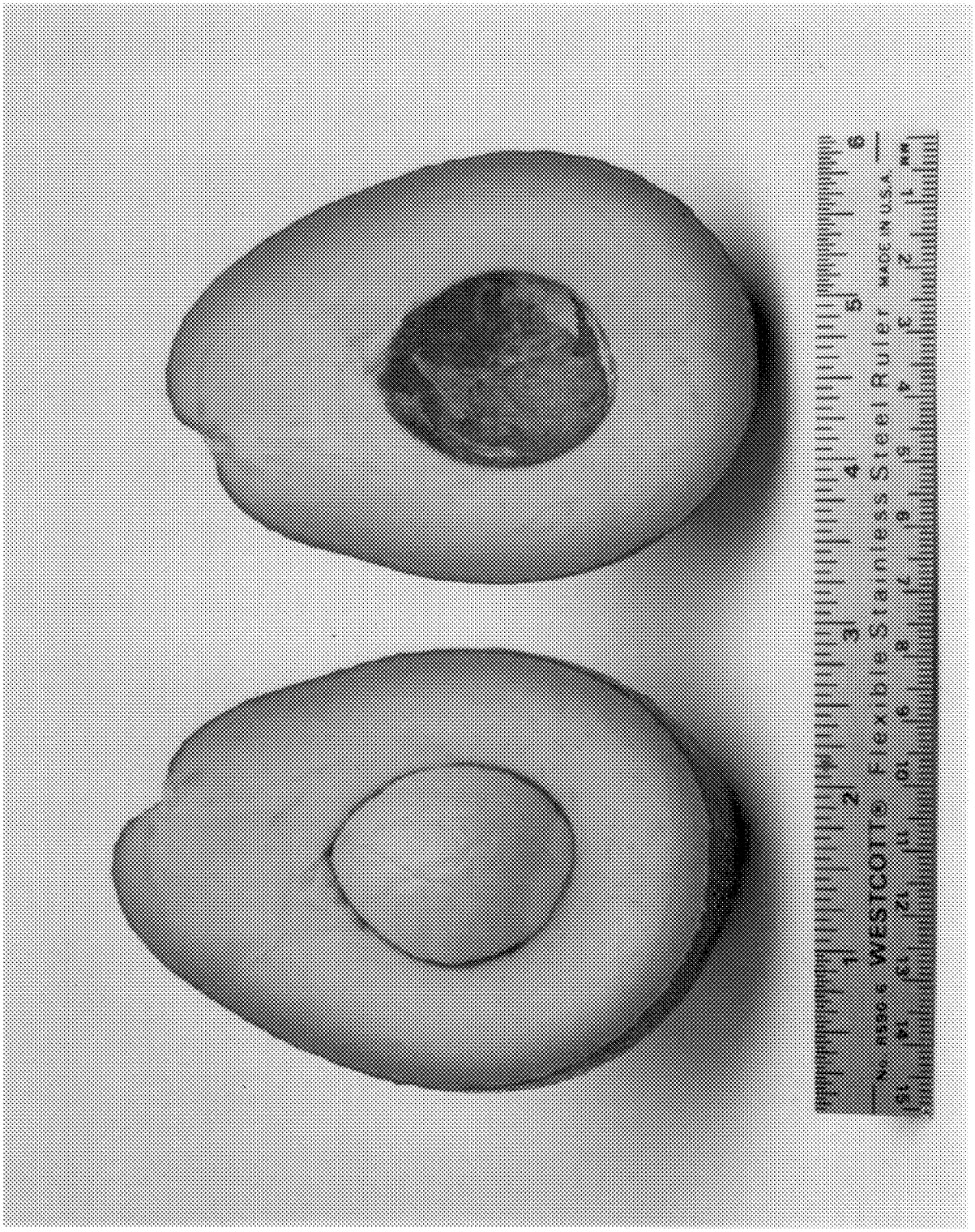
FIG. 2 shows a sagittal section of the fruit of FIG. 1, with the seed intact.
Figure 3:
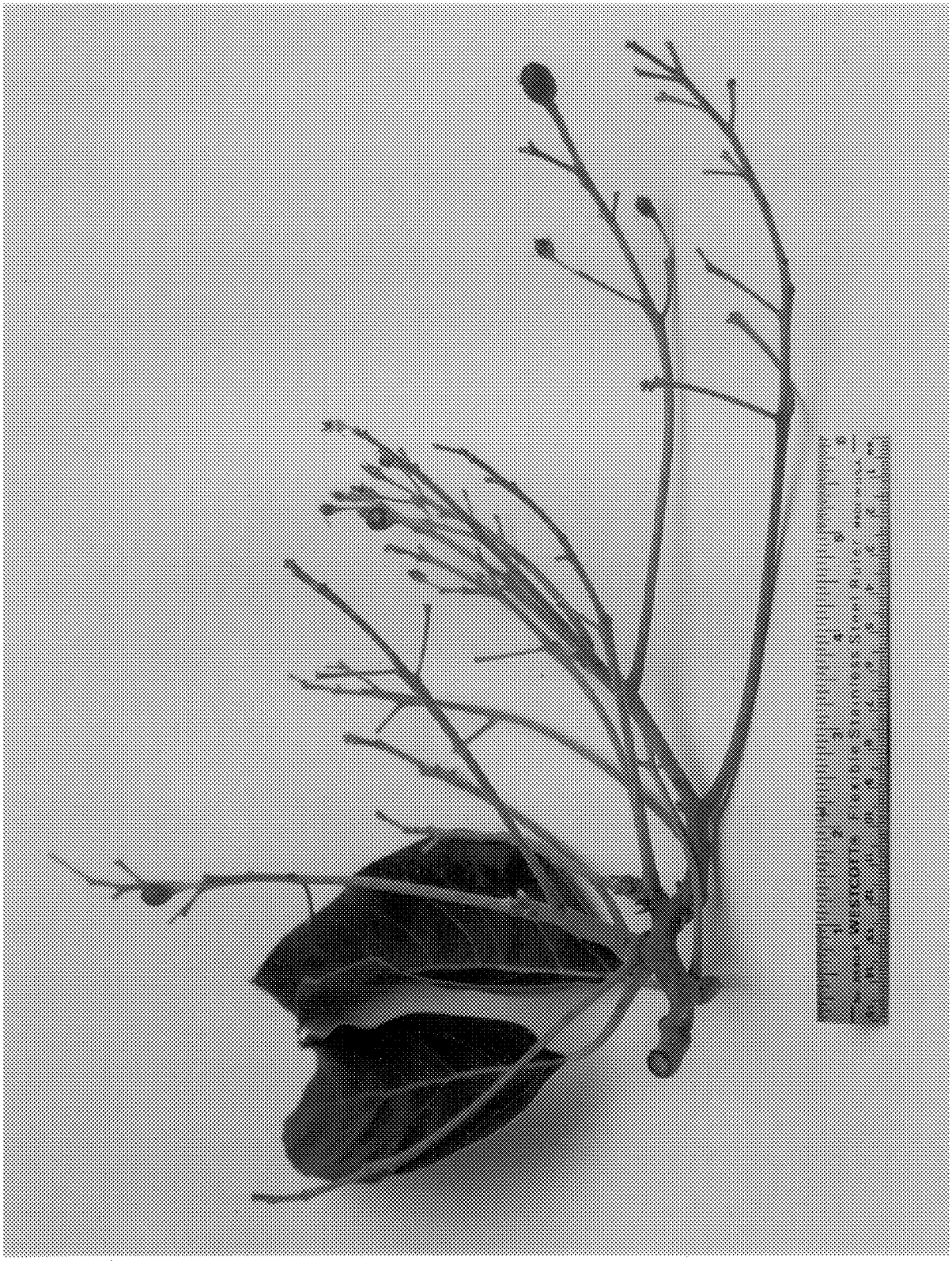
FIG. 3 shows a fruit set on an August/September bloom.
Figure 4:
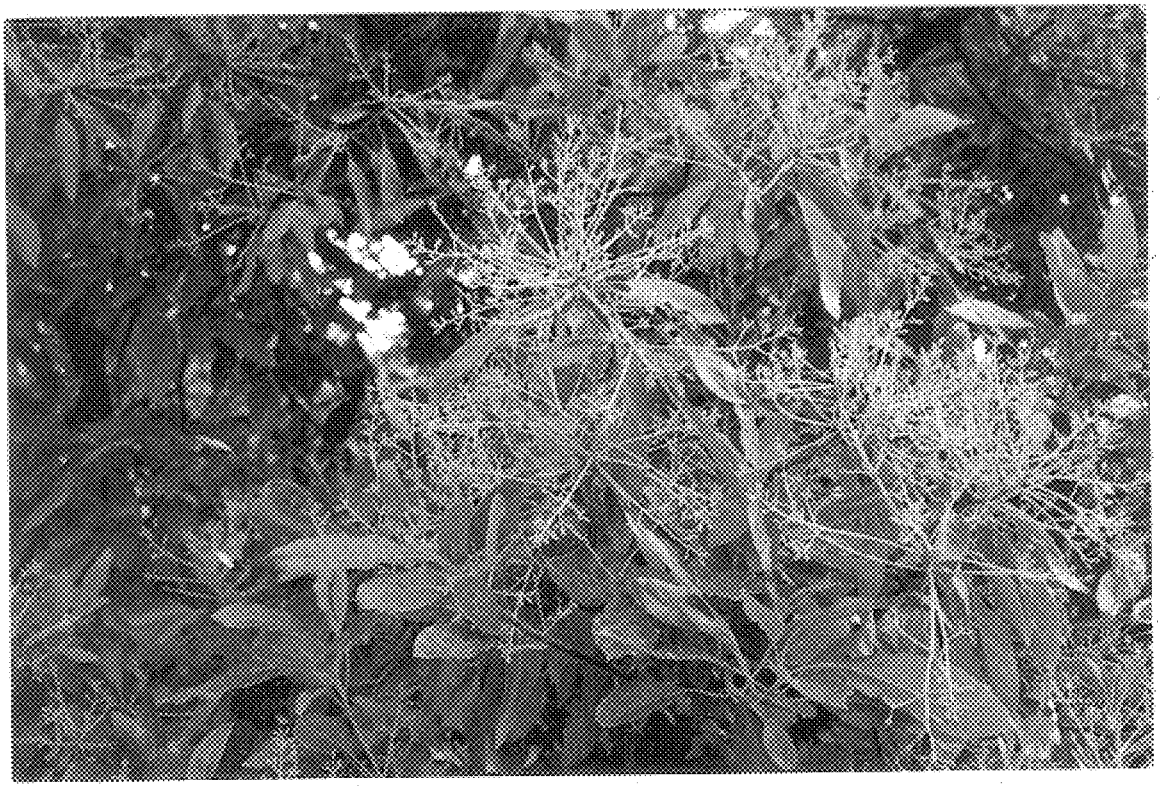
FIG. 4 shows 'Mendez No. 1' in normal bloom in California during August.
Figure 5:
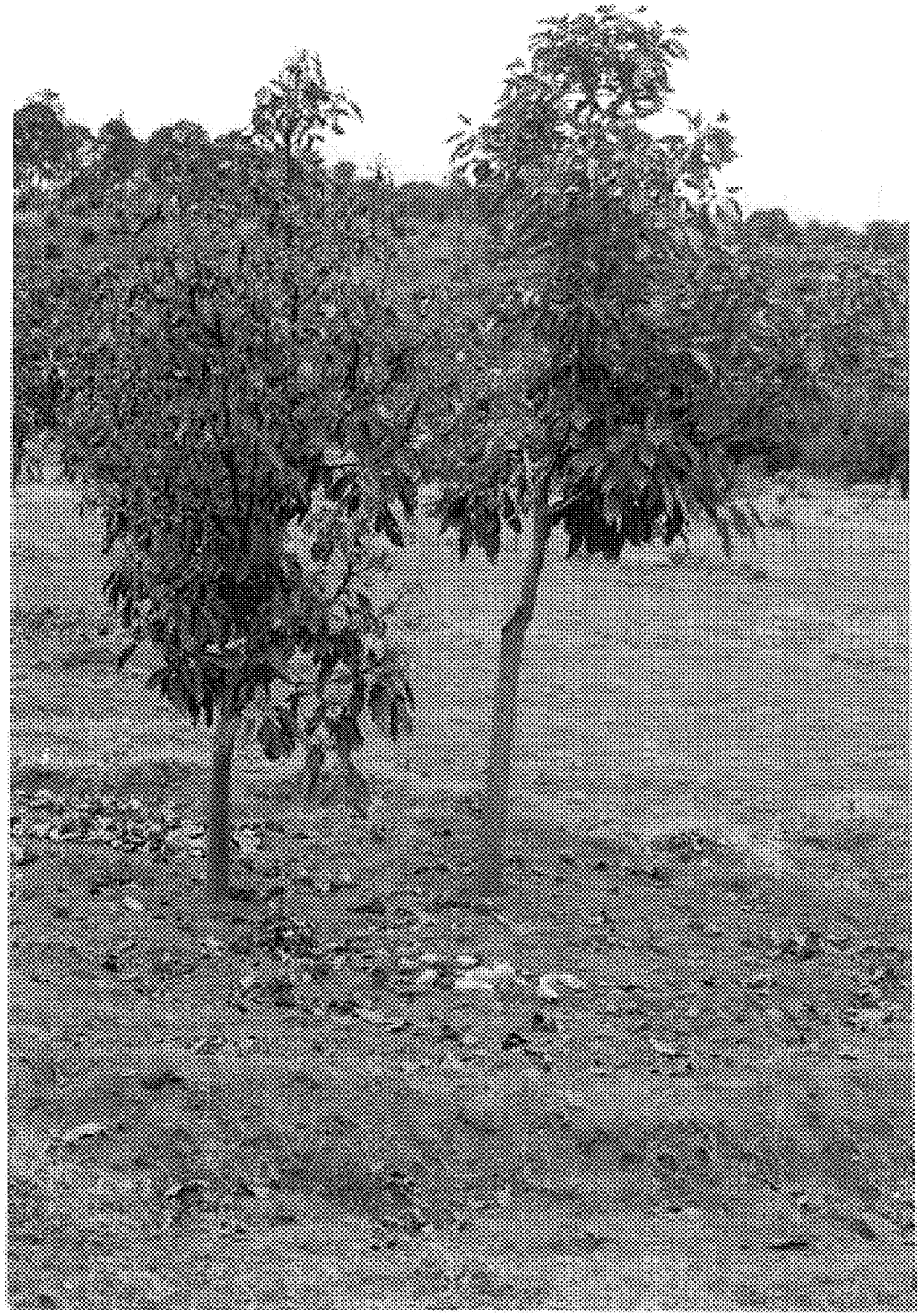
FIG. 5 shows a comparison of Mendez No. 1 (right) and Hass (left) avocado varieties in Michoacan, Mexico, after a frost, illustrating greater frost tolerance of the Mendez No. 1 variety.
Figure 6:
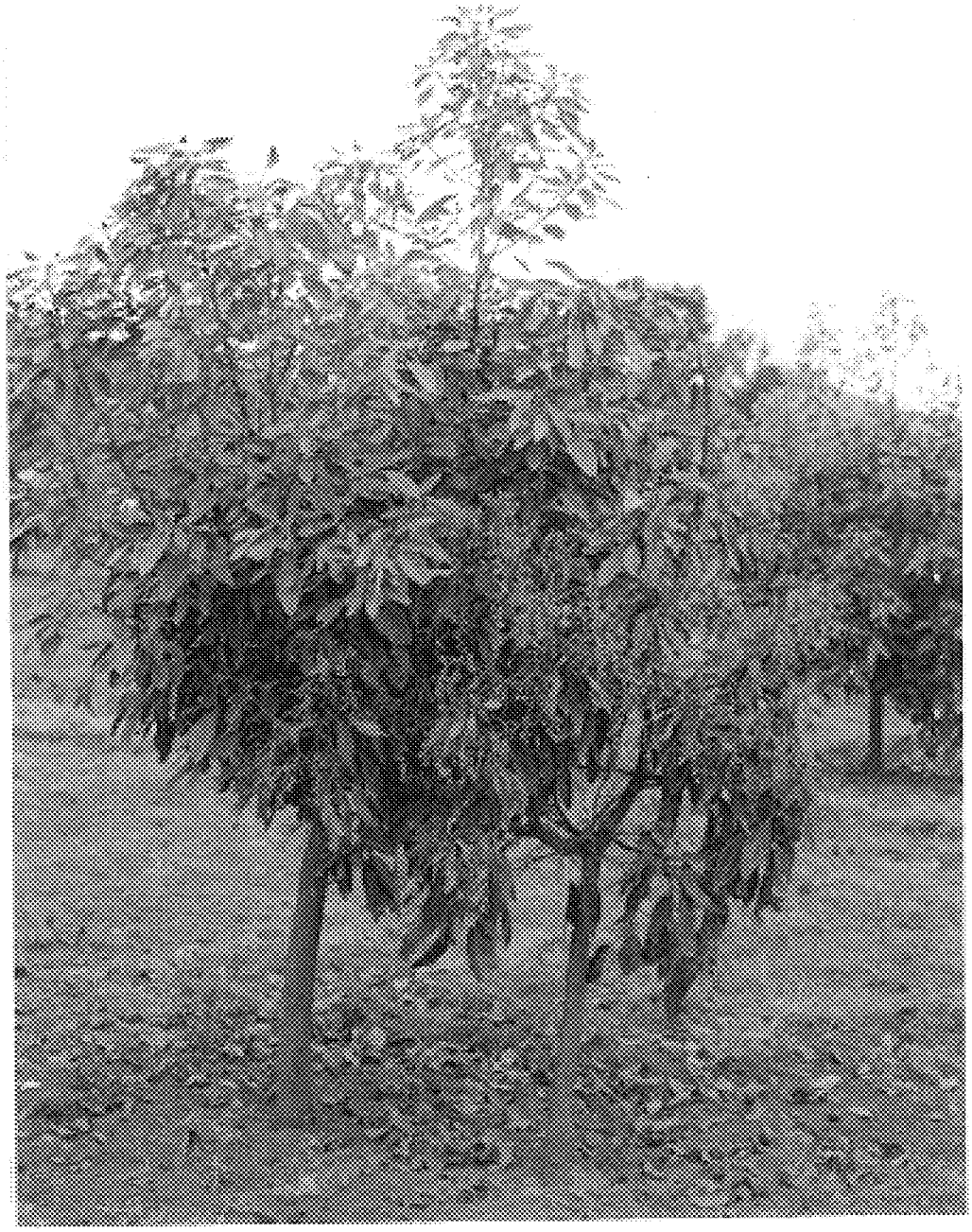
FIG. 6 shows a comparison of Mendez No. 1 (left) and Hass (right) avocado varieties in Michoacan, Mexico, after a frost, illustrating, different tolerances of the varieties.

In those instances where a precise color assessment can be made, reference is to the Munsell Book of Color. In other instances, general color terms are used in accordance with the ordinary dictionary significance.

Cultivar name: Mendez No. 1.

Botanical name: *Persea americana.*

Form: Tree.

Growth: Medium vigor, medium size, with a growth rate and habit similar to the 'Hass' avocado tree.

Wood: New wood: Normally green, smooth bark, without corky or specially pigmented lenticels. Old wood: Brown and corky as are most avocado varieties.

Disease: No known disease resistance, but quite vulnerable to parasitism by *Oligonychus perseae.*

Foliage:

*Type.*—Single leaf

*Size.*—Average, very similar to the Hass avocado variety. Leaves as small as 2" by ¾" to as large as 8½" by 3".

*Quantity.*—Abundant.

*Color.*—General: Very similar to the Hass avocado variety. Upper side of leaf: New foliage has reddish or copper colored shiny immature leaves which gradually expand and mature to a clean, large, medium green color as a growth flush terminates. Old foliage is dark green and fully expanded. Grayish olive green, 7.5 GY 3/2 Lower side of leaf: New foliage has reddish or copperish light green color, dull-finish leaves which gradually expand and mature to light green as a growth flush terminates. Old foliage is medium green dull-finish and fully expanded. Veins are prominent and in relief. Moderate olive green, 7.5 Gy 4/4.

*Shape.*—Broad lanceolate, as in the Hass avocado variety.

*Texture.*—Upper side smooth, shiny; lower side smooth, dull.

*Scent.*—Freshly crushed leaves normal for Guatemalan types, no noticeable anise odor typically found in Mexican varieties.

*Ribs and veins.*—Similar to the Hass variety.

*Edge.*—Smooth.

*Petiole Color.*—Strong yellow green, 2.5 GY 6/8

Fruit: Very good quality, similar to the Hass variety.

*Flesh Color.*—Brilliant yellow green, 2.5 GY 9/8

*Form.*—Pear to spheroidal.

*Aspect.*—Pebbly, as with the Hass avocado variety.

*Color at maturity.*—Moderate olive green, 7.5 GY 4/4, grading to black as maturity advances from acceptable quality to ideal maturity and beyond.

*Size at maturity.*—Depending upon the size of the crop on the tree, averages six to seven ounces per fruit. This is about one to one and one half ounces lighter than the Hass avocado variety. Typical fruit length is 3 ¼" to 3 ¾", the ratio of length to cross sectional diameter is approximately 1.35.

*Seeds*.—Medium size and shape.

*Seed Color*.—Moderate yellowish brown with coat, 10 R 3/4. Moderate orange yellow without coat, 7.5 YR 8/8.

*Blooming habit*.—Profuse normal blossoms approximately two months earlier than the Hass avocado variety in Michoacan, Mexico. In Uruapan, Michoacan the regular 'Hass' trees bloom in the spring up to and including March. The fall bloom, called "flor loca" in Spanish, and "off bloom" in English, begins in September. The Mendez No. 1 variety, on the other hand, blooms in Michoacan for four months from July to October. In California, the Mendez No. 1 variety blossoms in August and September and also in February. In California the Hass avocado variety normally blossoms only in March and April. Appearance of blossoms is indistinguishable from the Hass avocado variety, flowers are perfect with no unusual pollination requirements known.

*Harvesting*.—Early in the season the 'Mendez No. 1' fruit is normally harvested about two months earlier than the 'Hass' avocado fruit. In Michoacan, Mexico adult trees yield 150–200 pounds.

*Ripening*.—Normal for avocados. Indistinguishable from comparably mature 'Hass' avocado trees.

*Fruit Peeling*.—Easy peeling early in the season of its maturity. Peel is removed smoothly with minimum breaking and flaking, leaving no objectional residue on the surface of the flesh.

*Taste*.—Excellent. Indistinguishable from the Hass avocado variety.

Frost tolerance: Distinctly more frost tolerant than the Hass avocado variety. 'Mendez No. 1' tolerates frosty conditions such as 28° Fahrenheit for several hours or even 26° for two or three hours with less severe damage than by 'Hass'.

The tree and its fruit herein described may vary in slight detail due to climate or soil conditions under which the variety is grown.

What is claimed is:

1. A new and distinct variety of avocado tree named Mendez No. 1, as herein described and illustrated.

* * * * *